United States Patent [19]

Kondo et al.

[11] Patent Number: 4,548,816
[45] Date of Patent: Oct. 22, 1985

[54] ANTIBIOTIC SF-2288 AND ITS PREPARATION METHOD

[75] Inventors: Yasumitsu Kondo, Kawasaki; Takashi Shomura; Junko Yoshida, both of Yokohama; Kazuo Okano, Maebashi; Masaji Sezaki, Tokyo; Tatsuo Itoh, Isehara, all of Japan

[73] Assignee: Meiji Seika Kaisha, Ltd., Tokyo, Japan

[21] Appl. No.: 623,177

[22] Filed: Jun. 21, 1984

[30] Foreign Application Priority Data

Jun. 23, 1983 [JP] Japan .................................. 58-113519

[51] Int. Cl.$^4$ .................... A61K 35/74; C12P 1/06
[52] U.S. Cl. ........................................ 424/116; 435/169
[58] Field of Search ........................ 424/116; 435/169

Primary Examiner—Jerome D. Goldberg
Attorney, Agent, or Firm—James J. Ralabate

[57] ABSTRACT

Novel antibiotic SF-2288 is produced by fermentation of an actinomycete belonging to the genus Actinomadura in nutrient medium. Based on its physico-chemical and biological properties, antibiotic SF-2288 possesses an excellent antimicrobial activity against Gram-positive and Gram-negative microorganisms and antiviral activity.

2 Claims, 3 Drawing Figures

ANTIBIOTIC SF-2288 AND ITS PREPARATION METHOD

DETAILED DESCRIPTION OF THE INVENTION

Industrial Application of the Invention

The present invention relates to a novel antibiotic and its preparation method.

Purposes of the Invention

In the screening program for novel and useful antibiotics which are active against various microorganisms of Gram-positivity and Gram-negativity, the present inventors have discovered that an actinomycete belonging to the genus Actinomadura produces novel antibiotic SF-2288 in nutrient medium, and that, based on its physico-chemical and biological properties, antibiotic SF-2288 which possesses an excellent antimicrobial activity against Gram-positive and Gram-negative microorganisms and antiviral activity is concluded to be unknown in the literature.

Composition of the Invention

The present invention provides novel antibiotic SF-2288; its salts; and a preparation method thereof which consists of cultivating an SF-2288-producing microorganism belonging to the genus Actinomadura in medium whereby antibiotic SF-2288 or its salts are isolated from the broth.

An example of the antibiotic SF-2288-producing microorganisms according to the present invention is an actinomycete numbered SF-2288 that the present inventors have isolated from a soil sample collected near the Magome river in Shizuoka Prefecture.

The soil isolate SF-2288 have the following microbiological properties:

I. Morphology

Substrate mycelia elongate and branch well. The average diameter of mycelia is 0.5 micron. No segmentation of substrate mycelia is usually observed on agar media and in liquid media.

Aerial mycelia form poorly on usual agar media and relatively abundantly on oatmeal agar, with good sporulation. Aerial mycelium simply branches without verticilli. No sporangium, flagellated spore and sclerotium occur. The spore chain is straight, hooked or looped.

Under an electronic microscope, spores show the shape of ellipsoid or egg and an average size of 0.6−1.1×0.8−1.5 micron. The average number of spores in spore chains is 5-10. The surface of spores is smooth (slightly wrinkled).

II. Cultural characteristics on various agar media

The following table summarizes the cultural characteristics of actinomycete SF-2288 on various agar media: The description of color in bracket refers to Color Harmony Manual published by Container Corporation of America. The observations were recorded 14–21 days after inoculation at 28° C.

| Medium | Growth (reverse color) | Aerial mycelium | Soluble pigment |
|---|---|---|---|
| Sucrose-nitrate agar | very thin colorless | very poor white | none |
| Glucose-asparagine agar | very thin colorless | very poor white | none |
| Glycerol-asparagine agar | thin colorless | poor white | none |
| Starch agar | thin colorless–pale ivory (2 ca) | poor white | none |
| Yeast-starch agar | good pale melon yellow (3 ea)–pale apricot (4 ea) | white, slightly tinted with pink | none |
| Oatmeal agar | moderate-good colorless–pale apricot (4 ea) | white, slightly tinted with pink | none |
| Yeast-malt agar | good pale apricot (4 ea) | none | none |
| Tyrosine agar | thin–moderate pale ivory (2 ca) | poor white | none |
| Nutrient agar | thin–moderate yellowish brown (2 fb) | none | none |
| Bennett agar | good yellowish brown (2 fb) | none | none |

III. Physiological characteristics (1) Growth temperature: The actinomycete can grow in a temperature range from 15° C. to 42° C. on yeast-malt agar. The optimum growth temperature is 26° C.–37° C.

(2) Liquefaction of gelatin: Negative (20° C., 21 days of growth).

(3) Hydrolysis of starch: Positive.

(4) Reduction of nitrate: Positive.

(5) Peptonization of skim milk: Negative (28° C. and 37° C., 14 days of growth).

Coagulation of skim milk: Negative (28° C. and 37° C., 14 days of growth).

(6) Salt resistance: The organism can grow at 1.5% sodium chloride, but not at 3.0%.

(7) Formation of melanoid pigment: Negative.

IV. Utilization of carbon sources (in Pridham-Gottlieb agar medium)

(1) Utilizable: D-Glucose, D-fructose, D-xylose, L-arabinose, D-mannitol, L-rhamnose.

(2) Non-utilizable: i-Inositol, raffinose, sucrose, glycerol.

V. Cell wall composition

The hydrolysate of the whole cells of actinomycete SF-2288 revealed the presence of meso-diaminopimelate and madurose.

The microbial findings described above indicates that actinomycete SF-2288 belongs to the genus Actinomadura. Accordingly, the present inventors have designated the actinomycete numbered SF-2288 as Actinomadura sp. SF-2288.

The present actinomycete has been deposited with an accession number of FERM-P 7045 at the Fermentation Research Institute, Agency of Industrial Science and Technology, the Ministry of International Trade and Industry on Apr. 21, 1983, and transferred to the international deposition under the Budapest Treaty and accorded the international deposit number FERM BP-540 on June 14, 1984.

Like most actinomycetes, the actinomycete SF-2288 is genetically changeable with ultraviolet, X and radio-active rays and drugs, for example. All mutant strains, artificial or spontaneous, of Actinomadura sp. SF-2288 are employable in the method of the present invention, as far as they have an ability to produce antibiotic SF-2288.

In the method of the present invention, the said actinomycete is cultivated in usual media containing assimilable nutrient sources for most microorganisms. Particularly, common nutrient sources which have been used for cultivation of actinomycetes are usable. For example, glucose, starch, dextrin, sugar syrup, molasses, vegetable oils and animal oils are employable as the carbon sources. Soybean meal, wheat germ, meat extract, peptone, yeast extract, corn steep liquor, cottonseed meal, fish meal, ammonium sulfate, sodium nitrate and urea are good examples of the nitrogen sources. If necessary, calcium carbonate, sodium chloride, cobalt sulfate and phosphates may be added. Furthermore it is understandable that all organic and inorganic materials may be supplemented, as far as they promote the growth of the actinomycete and the production of antibiotic SF-2288.

The organism is cultivated under aerobic conditions and the submerged cultivation method is most preferred. Although the actinomycete can grow at a temperature of 15° C.–42° C., the cultivation is usually carried out at a temperature in the range of 26° C.–37° C.

In shaking and tank fermentations, the peak production of antibiotic SF-2288 is observed at a time point from 2 days to 10 days of cultivation depending on the medium composition and the fermentation conditions.

Antibiotic SF-2288 is bio-assayed using *Pseudomonas aeruginosa* as detector organism. With this assay microbe, a linear relation of the log concentration of antibiotic SF-2288 with the inhibition zone diameter is established in a concentration range of 250 μg/ml–2,000 μg/ml, giving an inhibition zone diameter from 11 mm to 17 mm.

As antibiotic SF-2288 has the physico-chemical properties detailed later, many isolation and purification methods are employable based on its physico-chemical properties. For example, the following isolation and purification procedure is efficient for preparation of antibiotic SF-2288:

The broth is mixed with a filter aid and is adjusted to pH 9 with 10N sodium hydroxide. After mycelia and solids are separated by filtration, the filtrate is passed through a column of cation exchange resin such as Amberlite IRC-50 ($NH_4^+$ form; Rohm and Haas Co.) and antibiotic SF-2288 is eluted from the column with 1N ammonia. The active eluate is again adsorbed on a column of Amberlite CG-50 ($NH_4^+$ form; Rohm and Haas Co.) and the antibiotic is eluted with 0.025–0.1N ammonia. If necessary, AviCel Cellulose (Funakoshi Pharmaceutical Co.) and anion exchange resin Dowex 1×2 ($OH^-$ form; Dow Chemical Co.), for example, are appropriately combined for column chromatographic purification of antibiotic SF-2288. Antibiotic SF-2288 may be isolated as free base, or, if required, as acid-addition salts with pharmaceutically acceptable inorganic acids such as hydrochloric acid, hydrobromic acid, sulfuric acid, nitric acid and phosphoric acid; and with pharmaceutically acceptable organic acids such as acetic acid, citric acid, benzoic acid and ascorbic acid.

The physico-chemical properties of antibiotic SF-2288 (free base) are described below.
1. Appearance: White, amorphous powder
2. Melting point: 161°–163° C. (darkened)
3. Elemental analysis: Carbon 39.61%, hydrogen 6.40%, nitrogen 8.89%
4. Infrared absorption spectrum:
   FIG. 1 is the infrared absorption spectrum of antibiotic SF-2288 in a KBr tablet.
   Infrared absorption spectrum of SF-2288 in a KBr tablet showed the characteristic absorptions at 3375, 2920, 1682, 1455, 1335, 1260, 1150, 1090, 1010 and 862 $cm^{-1}$.
5. $^1H$ and $^{13}C$ n.m.r. spectra:
   FIG. 2 is the $^1H$ n.m.r. spectrum of antibiotic SF-2288 measured in deutrium water at 200 MHz.
   FIG. 3 is the $^{13}C$ n.m.r. spectrum of antibiotic SF-2288 recorded in deutrium water at 50 MHz.
6. Specific optical rotation:
   $[\alpha]_D^{25} + 323.3°$ (c 1.0, water)
7. Electrophoretic nature: Basic;
   Antibiotic SF-2288 moves 8 cm toward the cathode in pyridine-acetate buffer, pH 6.4, (3,500 V, 15 minutes) ($Rm_{Lys}$ 0.9).
8. Molecular weight:
   Based on the titration equivalent at $PK_a'$ 7.1, the molecular weight of antibiotic SF-2288 is estimated to be $(159)_n$. It passes through Amicon Diaflo membrane YM5 (fractionating molecular weight 5,000), while about a fourth of the molecules passes through Diaflo membrane YM2 (fractionating molecular weight 1,000). Thus a molecular weight in the range of 1,000–5,000 is assumed for antibiotic SF-2288.
9. Solubility:
   Soluble in water; and hardly soluble in methanol, ethyl acetate, chloroform, benzene, and n-hexane.
10. Stability: Stable at a pH from 2 to 10
11. Rf values on cellulose thin layer chromatograms:
    Methanol/10% ammonium acetate (1/1): 0.63
    n-Propanol/pyridine/acetic acid/water (15/10/3/12): 0.0
    Chloroform/methanol/17% ammonia (2/1/1; upper phase): 0.23
12. Color reactions:
    Positive: Molisch, anthrone, Elson-Morgan, red tetrazolium, Graig-Liebach and ninhydrin reagents,
    Negative: Sakaguchi, Tollens and Fehling reagents Table 1 presents the antimicrobial activity of antibiotic SF-2288 on various microorganisms.

TABLE 1

| Antimicrobial spectrum antibiotic SF-2288 | |
|---|---|
| Test microorganisms | Minimum inhibitory concentration (μg/ml) |
| *Bacillus anthracis* No. 119 | 50 |
| *Escherichia coli* NIHJ JC-2 | 50 |
| *Staphylococcus aureus* 209P JC-1 | 12.5 |
| *Salmonella enteritidis* No. 11 | 200 |
| *Pseudomonas aeruginosa* IAM 1007 | 25 |

By the more investigation about effects of antibiotic SF-2288A, the present inventors have discovered that antibiotic SF-2288A gives anti-virus activities in vitro and in vivo as following experiments.

In the following, the experiments indicating the effects of the present anti-virus agent are explained.

Anti-virus activity (in vitro)

The anti-virus activities of antibiotic SF-2288A on three RNA viruses and two DNA viruses were examined.

(i) Tested viruses and cell lines
- (a) Influenza virus A/PR/8/34 strain—Vero cell
- (b) Newcastle disease virus (NDV) Miyadera strain—HeLa S3 cell
- (c) Vesicular stomatitis virus (VSV) New Jersey strain—L 929 cell
- (d) Vaccinia virus Lister strain—HeLa S3 cell
- (e) Herpes simplex virus (HSV) Type II, 196 strain—Vero cell (a), (b), (c): RNA virus
(d), (e): DNA virus (ii) Method Virus proliferation-inhibiting activity was assayed by cytophathic effect method (CPE method) with virus infection. Namely, each cells described above were prepared as $1\times10^5$/ml and poured 0.1 ml/well into 96 wells microplate. After cultivation at 37° C. for 48 hr in $CO_2$-incubator, the cells were once washed with PBS(−). According to the previously determined minimum degenerative concentrations (MDC) of antibiotic SF-2288A against each cells, MDC, $\frac{1}{2}$MDC and $\frac{1}{4}$MDC sample solutions (dissolved in MEM.FBS-2%) were poured 0.05 ml/well, viruses diluted with MEM.FBS-2% to 100 $TCID_{50}$/ml, 10 $TCID_{50}$/ml, 1 $TCID_{50}$/ml and 0.1 $TCID_{50}$/ml were inoculated 0.05 ml/well, and then cultivated at 36° C. in $CO_2$—incubator for 5 days. Cytopathic effects were observed by phase-contrast microscope, each $TCID_{50}$/ml were calculated and differences from virus controls ($\Delta$-log $TCID_{50}$/ml) were determined.

(iii) Result

| Sample | Dose μg/ml | $\Delta$-logTCID$_{50}$ | | | | |
|---|---|---|---|---|---|---|
| | | Influenza | NDV | VSV | Vaccinia | HSV |
| SF-2288A. free | 62.5 | — | 0.83 | — | 1.17 | — |
| | 31.2 | 0.50 | 0 | 1.30 | 1.17 | 1.83 |
| | 15.6 | 0.50 | 0 | 1.00 | 1.17 | 0.83 |
| | 7.8 | 0 | — | 1.16 | — | 0.10 |
| SF-2288A. HCl | 62.5 | — | 0.50 | — | ≧2.67 | — |
| | 31.2 | 0 | 0 | 0.50 | 1.17 | 1.83 |
| | 15.6 | 0 | 0 | 1.00 | 1.17 | 1.50 |
| | 7.8 | 0 | — | 0.50 | — | 1.83 |
| Virus control | TCID$_{50}$/ml | 5.50 | 9.50 | 6.50 | 4.67 | 6.50 |

Evaluation:
a: $\Delta$-logTCID$_{50}$/ml
$1.00 \leq a < 1.50$ - effective
$0.50 \leq a$ - slightly effective In the examination of proliferation-inhibiting activities on each viruses as mentioned above, antibiotic SF-2288A indicated activities on RNA viruses and DNA viruses. Especially, strong anti-virus effects were observed against DNA viruses (Vaccinia and HSV).

(iv) Result

| Sample Dose mg/kg | Inoculated virus titer pfu/ml | Mortalities and 50% survival days (ET$_{50}$) of mice after infection | | | | | | | | | | | | | | ET$_{50}$ days |
|---|---|---|---|---|---|---|---|---|---|---|---|---|---|---|---|---|
| | | Days after infection | | | | | | | | | | | | | | |
| | | 1 | 2 | 3 | 4 | 5 | 6 | 7 | 8 | 9 | 10 | 11 | 12 | 13 | 14 | |
| — | $10^4$ | | | | | | 20 | 60 | 90 | 90 | 90 | 90 | 100 | | | 7.00 |
| — | $10^3$ | | | | | | 10 | 10 | 30 | 40 | 50 | 50 | 50 | 60 | 60 | >9.91 |
| — | $10^2$ | | | | | | | | 10 | 10 | 10 | 10 | 10 | 10 | 10 | >15.0 |
| SF-2288A. free | | | | | | | | | | | | | | | | |
| 50 | $10^4$ | | | | | | 20 | 50 | 60 | 60 | 70 | 80 | 90 | 90 | 90 | 8.29 |
| 25 | $10^4$ | | | | | | | 40 | 40 | 60 | 80 | 80 | 80 | 80 | 80 | 9.00 |
| SF-2288A. HCl | | | | | | | | | | | | | | | | |
| 50 | $10^4$ | | | | | 10 | 10 | 50 | 60 | 60 | 90 | 90 | 90 | 90 | 90 | 7.83 |
| 25 | $10^4$ | | | | | | | 30 | 50 | 80 | 90 | 90 | 100 | 8.09 | | |
| IDU 150 | $10^4$ | | | | | | | 30 | 40 | 60 | 60 | 80 | 80 | 80 | 90 | 90 | 8.13 |

From the result of examination about mortality and 50% survival days (ET$_{50}$) of Herpes virus-infected mice as mentioned above, 10 to 30% survival mice were observed in each sample-treatment groups against virus-inoculated control group ($10^4$ pfu/ml) until 14 days after infection, and life prolongation effect was observed at range from 0.83 days to 2.0 days in 50% survival days. These values were also same level or more survival rate and life prolongation effect with that of the drug control IDU 150 mg/kg-treated group. Further, incidence of paralysis in dead mice of each sample-treatment groups were 1.5 days to 2 layers than that of virus-inoculated control group, and paralysis incidence rate reduction was also observed. Anti-herpes virus effect was observed also in vivo examination.

Anti-virus activity (in vivo)

The anti-virus activities of antibiotic SF-2288A on Herpes simplex virus were examined.

(i) Tested virus

Herpes simplex virus (HSV) Type II 196 strain was used at titer of $3.75\times10^6$ pfu/ml.

(ii) Animal

Ten male SLC-ICR mice at 4 weeks of age, mean weighing $20\pm0.5$ g, were used per group.

(iii) Method (a) Method of virus infection

Stock viruses were diluted with MEM to $10^4$ pfu/ml, $10^3$ pfu/ml and $10^2$ pfu/ml, and intraperitoneally inoculated at 0.1 ml/mouse. For the sample-treatment groups, $10^4$ pfu/ml virus were inoculated.

(b) Sample doses and administrating method

Both SF-2288A.free and SF-2288A.HCl were prepared as 50 mg/kg and 25 mg/kg, and control drug, 5-iodo-2'-deoxyuridine (IDU), was prepared as 150 mg/kg. Administration was performed intraperitoneally once in a day for 7 days, totally 7 times from 24 hr after inoculation of virus 0.1 ml/mouse. Incidence rate of paralysis, survival rate and prolongation of survival days were observed for 2 weeks.

Antibiotic SF-2288 that possesses the above-described physico-chemical and biological properties does not match any of the previously known antibiotics and thus it is concluded to be novel.

Accordingly the primary object of the present invention is to provide antibiotic SF-2288 as described above, and its acid-addition salts.

Toxicities of SF-2288

Death rate of mice in vivo

|  | 25 mg/kg | 100 mg/kg |
|---|---|---|
| SF-2288 free base | 0/3 | 1/3 |
| SF-2288 HCL salt | 0/3 | 0/3 |

Dosage to man

2–50 mg/kg per day by injection or suppository (EXAMPLES)

In the following, the present invention is explained in detail by examples.

Example 1

(1) Cultivation of actinomycete SF-2288

The seed medium for actinomycete SF-2288 contained 2.0% starch, 1.0% glucose, 0.6% wheat germ, 0.5% peptone, 0.3% yeast extract, 0.2% soybean meal and 0.1% calcium carbonate. The production medium consisted of 3.0% starch, 1.5% soybean meal, 1.0% wheat germ, 1.0% gluten meal, 0.5% meat extract, 0.25% sodium chloride and 0.3% calcium carbonate. The pHs of the media were adjusted to pH 7.0 prior to sterilization.

Three or four loopfuls each of the abundant culture of Actinomadura sp. SF-2288 (FERM BP-540) from yeast extract-starch agar slants were inoculated into two 100 ml-Erlenmeyer flasks containing 20 ml of the sterile seed medium and were cultivated under shaking at 28° C. for 4 days, providing the first seed culture.

Four milliliter each of the first seed culture was transferred into two 500-ml Erlenmeyer flasks containing 80 ml of the sterile seed medium and were grown with shaking at 28° C. for 3 days to give the second seed culture.

The third seed culture was produced by inoculating 50 ml each of the second seed culture to two 5-liter Erlenmeyer flasks containing 1 liter of the sterile seed medium; and cultivating the flasks at 28° C. for 3 days under shaking.

One flask each of the third seed culture was poured into two 50-liter jar fermentors including 35 liter of the sterile production medium and cultured for 6 days at 28° C. under forced aeration and agitation (aeration at 35 liter/minute and agitation at 270 rpm).

At the end of the fermentation, the broth was adjusted to pH 9.0 and filtered together with diatomaceous earth to yield 40 liter of the broth filtrate.

Example 2

Forty liter of the broth filtrate, pH 9.0, from Example 1 was passed through a 4-liter column of Amberlite IRC-50 ($NH_4^+$ form; Rohm and Haas Co.) so that antibiotic SF-2288 was retained on the resin. After washing with 20 liter of water, the column was eluted with 20 liter of 1N ammonia. The active eluate was concentrated to 2.0 liter under reduced pressure for removal of ammonia.

The concentrate was charged on a column of 200 ml of Amberlite CG-50 ($NH_4^+$ form; Rohm and Haas Co.). The column was rinsed one liter each of water, 0.025N ammonia and 0.05N ammonia; and then eluted with 0.1N ammonia. Active fractions from No. 15 to No. 28 (20 ml per fraction) were combined and concentrated to dryness under reduced pressure to give 1.04 g of a crude, pale yellow powder of antibiotic SF-2288.

Example 3

The crude powder (1.0 g) from example 2 was dissolved in a small volume of water and applied on a column of 120 ml of AviCel cellulose (Funakoshi Pharmaceutical Co.) which had been packed with 75% aqueous methanol. The column was rinsed with 600 ml of 75% aqueous methanol and then developed with 50% aqueous methanol, using a fraction volume of 5 ml. Active fractions from No. 10 to No. 17 were combined; and concentrated to dryness under reduced pressure to provide 460 mg of a crude, white powder of antibiotic SF-2288. Four hundreds milligram of this crude powder was dissolved in a small volume of water and adsorbed on a 400-ml column of Dowex 1×2 ($OH^-$ form; Dow chemical Co.). The elution of the antibiotic in 8-ml fraction volumes gave the antimicrobial activity in fraction Nos. 45–56. The active fractions were united and evaporated to dryness under reduced pressure. A white powder of antibiotic SF-2288 (free base; 168 mg) was obtained.

Figure 1:
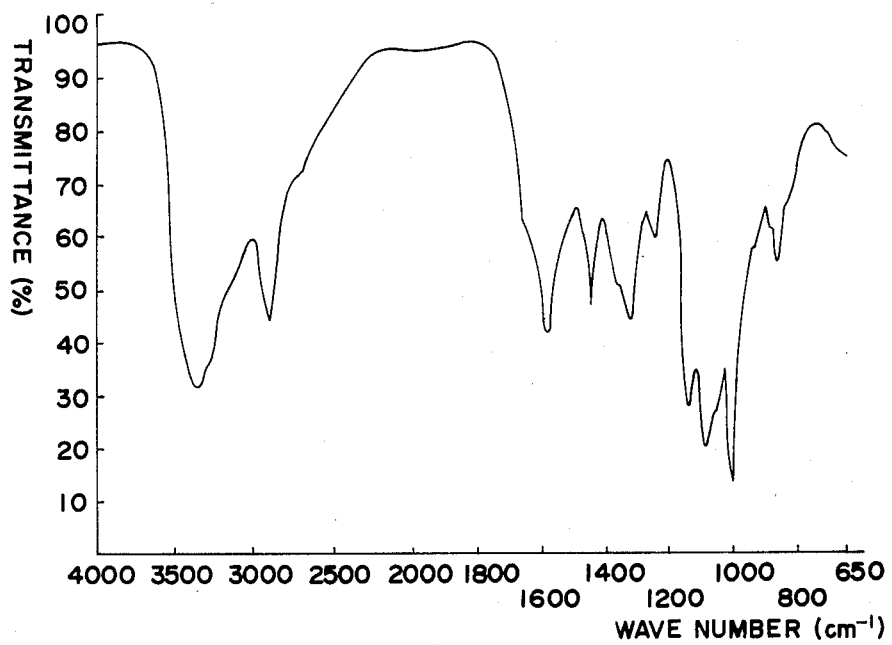
FIG. 1 is the infrared absorption spectrum of the free base of antibiotic SF-2288 (KBr tablet).
Figure 2:
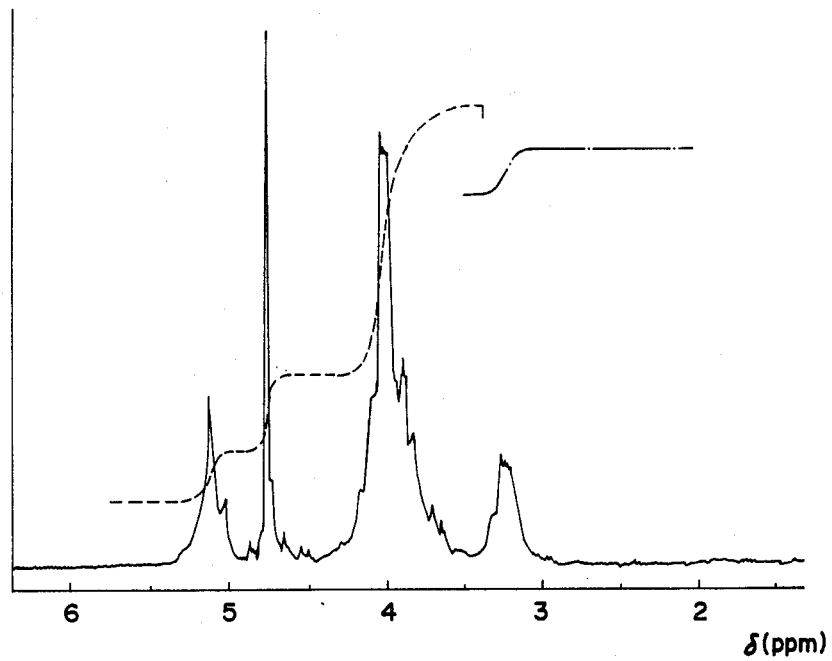
FIG. 2 is the $^1H$ n.m.r. spectrum of the free base fo antibiotic SF-2288 at 200 MHz (in deutrium water).

What is claimed is:

1. Antibiotic SF-2288 having the following properties as free base:
   (1) Appearance: White, amorphous powder
   (2) Elemental analysis: Carbon 39.61%, hydrogen 6.40%, nitrogen 8.89%, oxygen 45.10% (percentage by weight)
   (3) Specific optical rotation: $[\alpha]_D^{25} +323.3°$ (c 1.0, water)
   (4) Solubility: Soluble in water and hardly soluble in methanol, ethyl acetate, chloroform, benzene and n-hexane
   (5) Infrared absorption spectrum: Infrared absorption spectrum of SF-2288 in a KBr tablet showed the characteristic absorptions at 3375, 2920, 1682, 1455, 1335, 1260, 1150, 1090, 1010 and 862 $cm^{-1}$
   (6) $^1H$ n.m.r. spectrum: The spectrum in $D_2O$ is shown in FIG. 2

Figure 3:
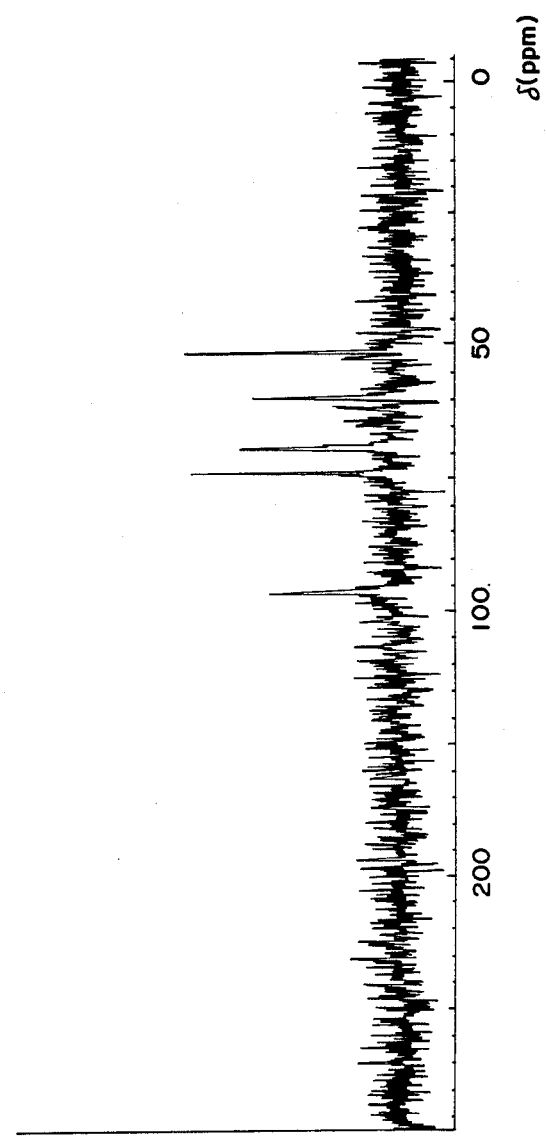
FIG. 3 is the $^{13}C$ n.m.r. spectrum of the free base of antibiotic SF-2288 at 50 MHz (in deutrium water).

(7) $^{13}$C n.m.r. spectrum: The spectrum in $D_2O$ is shown in FIG. 3

(8) Electrophoretic nature: Basic; It moves 8 cm toward the cathode in pyridine-acetate buffer, pH 6.4 (3,500 V, 15 minutes); $RM_{Lys}$ 0.9

(9) Rf values on cellulose thin layer chromatograms: Methanol/10% ammonium acetate (1/1): 0.63; n-Propanol/pyridine/acetic acid/water; (15/10/3/12): 0.0; Chloroform/methanol/17% ammonia (2/1/1; upper phase): 0.23

(10) Color reactions:

Positive: Molisch, anthrone, Elson-Morgan, red tetrazolium, Graig-Liebach and ninhydrin reagents Negative: Sakaguchi, Tollens and Fehling reagents.

2. The process for producing the antibiotic SF-2288 as defined in claim 1 which comprises culturing Actinomadura sp. SF-2288 under submerged aerobic conditions in a nutrient medium containing a carbon source and a nitrogenous nutrient until a substantial amount of antibiotic SF-2288 is produced by said organism in said nutrient medium and recovering the antibiotic from the nutrient medium substantially free of substances co-produced therewith.